(12) United States Patent
Arnold et al.

(10) Patent No.: US 6,448,013 B1
(45) Date of Patent: Sep. 10, 2002

(54) DUPLEX PROBES FOR HYBRIDIZATION REACTIONS

(75) Inventors: Lyle Arnold, Poway, CA (US); Tod Bedilion, San Carlos, CA (US); Erik Bieldanes, Lafyette, CA (US); Thomas P. Theriault, Pasadene, CA (US); Warren Lei, Fremont, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/721,801

(22) Filed: Nov. 22, 2000

Related U.S. Application Data (63) Continuation of application No. 09/586,156, filed on Jun. 2, 2000, which is a continuation of application No. 09/449,059, filed on Nov. 24, 1999.

(51) Int. Cl.$^7$ .................... C12Q 1/68; C12P 19/34; G01N 33/00; C07H 21/02; C07H 21/04
(52) U.S. Cl. .................. 435/6; 435/91.1; 435/91.2; 436/94; 536/23.1; 536/24.3; 536/24.33
(58) Field of Search ................. 435/6, 91.1, 91.2, 435/283.1, 287.1, 287.2, 183; 436/94; 536/23.1, 24.3, 24.33, 25.3

(56) References Cited

U.S. PATENT DOCUMENTS

| | | | |
|---|---|---|---|
| 5,384,261 A | | 1/1995 | Winkler et al. |
| 5,445,934 A | | 8/1995 | Foder et al. |
| 5,532,128 A | | 7/1996 | Eggers et al. |
| 5,541,311 A | * | 7/1996 | Dahlberg et al. .......... 536/23.7 |
| 5,700,637 A | | 12/1997 | Southern |
| 5,807,522 A | * | 9/1998 | Brown et al. ................. 422/50 |
| 5,888,737 A | * | 3/1999 | DuBridge et al. ............. 435/6 |
| 5,888,742 A | | 3/1999 | Lal et al. |
| 5,891,669 A | * | 4/1999 | Jensen et al. .............. 435/69.1 |
| 5,891,674 A | | 4/1999 | Hillman et al. |
| 5,948,897 A | * | 9/1999 | Sen et al. .................. 536/22.1 |
| 5,976,790 A | | 11/1999 | Pinkel et al. |
| 6,013,449 A | | 1/2000 | Hacia et al. |

FOREIGN PATENT DOCUMENTS

| | | |
|---|---|---|
| WO | 92/11390 | 7/1992 |
| WO | 95/11995 | 5/1995 |
| WO | 95/25116 | 9/1995 |
| WO | 99/55916 | 11/1999 |

OTHER PUBLICATIONS

Sen et al., A sodium–potassium switch in the formation of four–stranded G4–DNA.. Nature, 344, 410–414, 1990.*
Sen et al., Novel DNA superstructures formed by telomere–like oligomers. Biochemistry, 31, 65–70, 1992.*
Sen et al., Guanine Quarter Structure. Methods in Enzymology, 211, 191–199, 1992.*
Venczel.et al., Parallel and antiparallel G–DNA structures from a complex telomeric sequence. Biochemistry, 32, 6220–6228, 1993.*

(List continued on next page.)

*Primary Examiner*—W. Gary Jones
*Assistant Examiner*—Frank Lu
(74) *Attorney, Agent, or Firm*—Richard Aron Osman (57) ABSTRACT

Methods are provide for quantitatively determining the amount of polynucleotides in a sample. In one method, the distinct polynucleotide targets and standard polynucleotide targets are contacted with detectable probes and independently detectable single or double stranded complements to the standard targets under hybridization conditions. The hybridization pattern from the probe is compared to the hybridization pattern from the standard sequences to obtain quantitative information about the genetic profile of the labeled nucleic acid sample. Also provided are kits for the use of the methods.

25 Claims, 9 Drawing Sheets

OTHER PUBLICATIONS

Chou et al., Affinity methods for purification of DNA sequencing reaction products for mass spectrometric analysis. Rapid Communication Mass Spectrometry, 10, 1410–1414, 1996.*

Boehringer Mannheim Biochemicals, Nonradioactive in Situ Hybridzation Application Manual (1992), Chapter III, p. 1.*

Proudnikov et al. 1998, Analytical Biochemistry 259:34–41.

New England Biolabs Catalog (19976/97), p. 82, published by New England Biolabs, Inc. 32 Tozer Road, Beverly, MA 01915–5599.*

Speicher et al. 1996 Karyotyping human chrmosomes by combinatorial multi–fluor FISH. Nature Genet. 12, 368–75.

PCR: A Practical Approach 1991 p. 77–83, Eds. M.J. McPherson et al., Oxford University Press.

Nucleic Acid hybridization: a practical approach 1985 p. 86–109, Ed. Haemes, BD and Higgins, SJ. IRS Press Limited.

Tyagi et al., Molecular beacons: Probes the fluoresce upon hybridization. Nature Biotech. 14, 303–308, Mar. 1996.

Schena et al., Parallel human genome analysis: Microarray–based expression monitoring of 1000 genes. Proc. Natl. Acad. Sci. USA 93, 10614–10619, Oct. 1996.

Huang et al., Characterization of a genomic hybrid specifying the human erythrocyte antigen Dantu: Dantu gene is duplicated and linked to a beta glycophorin gene deletion. Proc. Nat. Acad. Sci. USA 85, 9640–9644, Dec. 1998.

Sokol et al., Real time detection of DNA–FNA hybridization in living cells. Proc. Natl. Acad. Sci. USA 95, 11538–11543, Sep. 1998.

Au et al., Single–step hybridization screening for recombinant DNA clones with correct insert orientation and intact junction using a junctional oligonucleotide probe. Proceedings of the National Science Council, ROC, Part B: life Sciences, 20,27–30, 1996.

Lockhart, D.J. et al., Expression monitoring by hybridization to high–density oligonucleotide arrays, Nat. Biotech. 14:1675–1680, 1996.

Bates et al., Detection and kinetic studies of triplex formation by oligonucleotide using real–time biomolecular interaction analysis (BIA. Nucleic Acids Res. 23, 3627–3632, 1995.

Ellouze et al., Use of fluorescein–labeled oligonucleotide for analysis of formation and dissociation kinetics of T:A:T triple–stranded DNA: effect of divalent cations. J. Biochem. 121, 521–526, 1997.

Pease et al., Light–generated oligonucleotide arrays for rapid DNA sequence analysis. Proc. Natl. Acad. Sci. USA 91, 5022–5026, 1994.

* cited by examiner

```
                          SEQUENCE LISTING

<160> NUMBER OF SEQ ID NOS: 4

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 1
ttcgagcttg gcgtaatcat ggtcatagct gtttcctgtg tgaaattgtt atccgctca      59

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
tgagcggata acaatttcac acaggaaaca gctatgacca tgattacgcc aagctcgaa      59

<210> SEQ ID NO 3
<211> LENGTH: 99
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
gtaatcatgg tcatagctgt ttcctgtgtg aaattgttat ccgctcattt tttgagcgga    60
taacaatttc acacaggaaa cagctatgac catgattac                           99

<210> SEQ ID NO 4
<211> LENGTH: 98
<212> TYPE: DNA
<213> ORGANISM: Artificial Sequence
<220> FEATURE:
<223> OTHER INFORMATION: Description of Artificial Sequence: Synthetic
      Sequence
```

-continued

```
<400> SEQUENCE: 4
gagcggataa caatttcaca caggaaacag ctatgaccat gattactttt tgtaatcatg      60
gtcatagctg tttcctgtgt gaaattgtta tccgctca                             98
```

DUPLEX PROBES FOR HYBRIDIZATION REACTIONS

CROSS-REFERENCE TO RELATED APPLICATION

This application is a continuation of under 35USC120 to U.S. Ser. No. 09/586,156, filed by the same inventors on Jun. 2, 2000, which is a continuation of and claims priority to U.S. Ser. No. 09/449,059, filed by the same inventors on Nov. 24, 1999.

FIELD OF INVENTION

The present invention relates to polynucleotide hybridization.

BACKGROUND OF THE INVENTION

Hybridization is a powerful and versatile technique for sequencing, detecting and localizing nucleic acids. In the general area of molecular biology, hybridization is used to map genes, detect gene expression and over-expression, diagnose diseases, identify pre-disposition to diseases, and the like. In general, labeled nucleic acid probes are hybridized to target samples and hybridization then detected. Numerous isotopic and non-isotopic systems have been developed to visualize labeled DNA probes including fluorescence-based direct detection methods, the use of digoxigenin- and biotin-labeled DNA probes coupled with fluorescence detection methods or anti-body-enzyme detection methods.

The target samples can be in solution or they can be immobilized on a solid surface, such as in arrays and microarrays. In microarrays, a typical method of using microarrays involves contacting nucleotide sequences contained in a fluid with the sequences immobilized on the microarrays under hybridization conditions, and then detecting the hybridization complex. The resultant pattern of hybridized nucleic acids provides information regarding the genetic profile of the sample tested. A widely used method for detecting the hybridization complex in microarrays is by fluorescence. In one method, probes derived from a biological sample are amplified in the presence of nucleotides that have been coupled to a fluorescent label (reporter) molecule so as to create labeled probes, and the labeled probes are then incubated with the microarray so that the probe sequences hybridize to the complementary sequences immobilized on the microarray. A scanner is then used to determine the levels and patterns of fluorescence.

The use of fluorescence detection in microarray analysis is disclosed in U.S. Pat. No. 5,888,742 to Lal et al. for the detection of altered expression of human phospholipid binding protein (PLBP) and in U.S. Pat. No. 5,891,674 to Hillman et al. for the monitoring of the expression level of insulin receptor tyrosine kinase substrate (IRS-p53h), and to identify its genetic variants, mutations and polymorphisms for determining gene function, and in developing and monitoring the activity of therapeutic agents.

The current hybridization methodology is generally capable of providing qualitative information only since the labels and labeling schemes used in current methodologies yield a signal that is non-quantitative. For example, in microarrays, the signal is affected by the sample to sample variation in printing, the quality and hybridization performance of each array element, and the like. One method of obtaining "quantitative" information, that could measure variations such as synthesis or spotting performance, hybridization performance, local noise, and the like, entails comparing the signal of interest to the signal for other genes or sequences on the microarray that act as "controls." Such methods, however, still do not yield true quantitative information of a particular target in a sample. As such, there continues to be interest in the development of new methodologies capable of yielding quantitative information from hybridization reactions.

SUMMARY OF THE INVENTION

Methods are provided for normalizing and quantitating hybridization reactions. In the subject methods, distinct polynucleotide targets and standard polynucleotide targets are contacted with detectable nucleic acid probes complementary to the distinct targets and independently detectable complements to the standard targets to produce a hybridization pattern. The hybridization pattern is then detected and used to obtain information, including quantitative information, about the amount of polynucleotides in a sample or deposited on the microarray. The independently detectable standard probes can be single stranded or double stranded. The single stranded standard probes can be sense or anti-sense, and the double stranded standard probes are sense and antisense to the standard targets. Preferably, the sense and anti-sense complements are present in approximately equimolar concentration. Alternatively, the double stranded probe can be a hairpin duplex wherein the sense and anti-sense strands are covalently attached.

These and other objections, advantages, and features of the invention will become apparent to those persons skilled in the art upon reading the details of the invention as more fully described below.

DETAILED DESCRIPTION

Before the present methods and kits are described, it is to be understood that this invention is not limited to particular methods and kits described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

DEFINITIONS

It must be noted that, as used in the specification and the appended claims, the singular forms "a, " "an" and "the" include plural referents unless the context clearly dictates otherwise. Thus, for example, reference to "a probe" means that more than one such probe can be present in the composition. Similarly, reference to "a microarray element" or "the microarray element" includes the possibility of one or more microarray elements, and the like.

The term "fluorescent" refers to the property of a substance (such as a fluorophore) to produce light while it is being acted upon by radiant energy, such as ultraviolet light, visible light, or x-rays.

The term "fluorescent label" refers to a compound comprising at least one fluorophore bonded to a probe or a microarray element.

The term "probe" or "sample probe" refers to a molecule that is recognized by its complement or a particular microarray element. Examples of probes that can be investigated by this invention include, but are not limited to, DNA, RNA, oligonucleotides, oligosaccharides, polysaccharides, sugars, proteins, peptides, monoclonal antibodies, toxins, viral epitopes, hormones, hormone receptors, enzymes, enzyme substrates, cofactors, and drugs including agonists and antogonists for cell surface receptors.

The term "target", "DNA element" or "microarray element" refers to a molecule that has an affinity for a given sample. Elements may be naturally occurring or synthetic molecules, and may be attached, covalently or noncovalently, to a surface, either directly or via a specific binding substance. Examples of elements which can be employed by this invention include, but are not restricted to, DNA, RNA, oligonucleotides, analogs, etc.

The term "complementary" or "complementarity", as used herein, refer to the natural binding of polynucleotides under permissive salt and temperature conditions by basepairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. Thus, the element and its probe, and the contact area between the element and the probe can be described as complementary.

The term "hybrid" refers to the product of a hybridization procedure between a probe and a microarray element as a result of complementarity.

The term "fragment", "segment" or "DNA fragment" refers to a portion of a larger DNA polynucleotide or sequence such as occurs in one chromosome or one region of a chromosome.

The term "gene expression" refers to the quantity or amount of specific mRNA transcribed from a specific gene.

The term "microarray" refers to an array of distinct polynucleotides or oligonucleotides synthesized or attached or deposited on a substrate, such as paper, nylon or other type of membrane, filter, chip, glass slide, beads, or any other suitable solid support, at high density.

The term "antisense" refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription.

In one embodiment, distinct polynucleotide targets and standard polynucleotide targets are contacted with a sample of labeled nucleic acids probes and independently detectable standard probes under hybridization conditions to produce a hybridization pattern.

In another embodiment, the distinct and standard polynucleotide targets are co-arrayed to the same location on an array or a microarray. The array or the microarray is contacted, under hybridization conditions, with a fluid sample containing labeled nucleic acid probes complementary to the distinct polynucleotide targets and independently detectable standard probes complementary to the standard sequences.

The standard polynucleotide and the distinct polynucleotide can be covalently attached, and then contacted with the sample of probes or arrayed as discrete array elements before being contacted with the sample of probes. The differently labeled standard probes can be single stranded or can have the sense and the anti-sense strands present in about equimolar concentration or can have the sense and anti-sense strands joined covalently, for example as a hairpin. After hybridization, the fluorescence measurement corresponding to the amount of standard probe hybridized with the standard sequences is used as a control signal to quantify the level of hybridization at each arrayed element. This information is useful in determining gene function, understanding the genetic basis of disease, diagnosing disease, and in developing and monitoring the activity of therapeutic agents (Heller, R. et al. (1997) Proc. Natl. Acad. Sci. 94:2150–55) .

The microarray is prepared and used according to the methods described in PCT application WO95/11995 (tiling strategies, Chee et al.), Lockhart, D. J. et al. (in situ synthesis by photolithography and oligonucleotide chemistry, 1996; Nat. Biotech. 14:1675–1680) and Schena, M. et al. (microdeposition, 1996; Proc. Natl;. Acad. Sci. 93:10614–10619), all of which are incorporated herein in their entirety by reference.

The microarray elements are capable of sequence specific hybridization with the nucleic acids of the sample. The microarray elements may comprise polynucleotides or hybridizing analogues or mimetics thereof, including: nucleic acids in which the phosphodiester linkage has been replaced with a substitute linkage, such as phosphorothioate, methylimino, methylphosphonate, phosphoramidate, guanidine and the like; nucleic acids in which the ribose subunit has been substituted, e.g. hexose phosphodiester; peptide nucleic acids, and the like. For a certain type of microarray, it may be preferable to use, as the targets, oligonucleotides which are only 7–10 nucleotides in length. The polynucleotide microarray elements may be single or double stranded, and may be PCR fragments amplified from cDNA. The microarray may contain polynucleotides which cover the known 5' or 3' sequence, sequential polynucleotides which cover the full length sequence, or unique oligonucleotides selected from particular areas along the length of the sequence. Polynucleotides used in the microarray may be oligonucleotides that are specific to a gene or genes of interest in which at least a fragment of the sequence is known, or that are specific to one or more unidentified cDNAs which are common to a particular cell type, developmental or disease state.

In the subject method, the standard sequences can be from a cloning vector, a oligonucleotide, or a polynucleotide. The standard sequences are preferably about 5–1000 nucleotides in length, more preferably about 20–80 nucleotides in length, most preferably about 50–70 nucleotides in length. In one aspect, the standard sequence is covalently attached to the distinct polynucleotide sequence. The attachment can be the 5' terminus, at the 3' terminus, or any continuous region within the microarray element, and can be overlapping or non-overlapping with the PCR primer. The covalent attachment may be the result of the cloning process, or may be synthetically or enzymatically ligated to the distinct sequence. When the hybridization reaction is carried out in solution, each sample preferably contains one distinct polynucleotide target, and each sample contains a standard polynucleotide sequence. When the hybridization reaction is carried out on arrays and microarrays, each of the elements includes a standard polynucleotide sequence. Each element can have the same standard sequence so that the microarray has a common standard polynucleotide sequence. Alternatively, each element can have a different standard sequence such that for a total number of n elements on the microarray, there are n−1 different standard sequences. In another aspect, the distinct polynucleotide targets and the standard polynucleotide targets can be co-arrayed at the same location on the array or the microarray. The distinct polynucleotides and the standard sequences can be co-arrayed in equimolar concentration or any other predetermined and known stoichiometry.

The substrates with which the polynucleotide microarray elements are stably associated may be fabricated from a variety of materials, including plastics, ceramics, metals, gels, membranes, glasses, beads, and the like. The arrays may be produced according to any convenient methodology, such as preforming the polynucleotide microarray elements and then stably associating them with the surface. A number of different array configurations and methods for their production are known to those of skill in the art and disclosed in U.S. Pat. No. 5,445,934 (in situ synthesis by photolithography), U.S. Pat. No. 5,532,128 (solid phase detection by electrical distribution differential); U.S. Pat. No. 5,384,261 (in situ synthesis by mechanically directed flow paths); and U.S. Pat. No. 5,700,637 (synthesis by spotting, printing or coupling); the disclosure of which are herein incorporated in their entirety by reference.

Alternatively, the polynucleotide microarray elements comprising the unique gene specific sequence and the standard sequences may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devices (slot blot or dot blot apparatus), materials (any suitable solid support), and machines (including robotic instruments) and may contain, for example, 8, 24, 96, 384, 1536 or 6144 oligonucleotides, or any other multiple between two and one million which lends itself to the efficient use of commercially available instrumentation.

In order to conduct sample analysis using the microarrays, the RNA or DNA from a biological sample is made into hybridization probes. The probe nucleic acids will generally be a DNA that has been reverse transcribed from RNA derived usually from a naturally occurring source, where the RNA could be total RNA, PolyA+mRNA, amplified RNA and the like. The initial mRNA sample may be derived from a physiological source including a single celled organism such as yeast, from a eukaryotic source, or a multicellular organism including plants and animals, particularly mammals and organs, tissues, and cells derived from the mammals such as from any bodily fluids (such as blood, urine, saliva, phlegm, gastric juices, etc.), cultured cells, biopsies, or other tissue preparations. Methods of isolating RNA from cells, tissues, organs or whole organisms are known to those of skill in the art and are described in Maniatis et al., Molecular Cloning: A Laboratory Manual (Cold Spring Harbor Press) (1989).

The MRNA is isolated, and cDNA is produced and used as probes for hybridizing to the targets. The probes may be labeled with radioisotopes, chemiluminescent compounds, heavy metal atoms, spectroscopic markers, magnetic markers, linked enzymes, fluorescent labels, and the like. A fluorescent label may be introduced into the probe directly as dye-bearing nucleotides, or bound after amplification using dye-streptavidin complexes to incorporated biotin containing nucleotides. For DNA produced by asymmetric PCR, fluorescent dye is linked directly to the 5' end of the primer. The fluorescent labels are chosen such that they absorbs light at wavelengths greater than 250 nm, preferably at wavelengths greater than about 350 nm, and fluoresce at wavelengths about 10 nm higher than the absorption wavelength. The fluorescent label may, for example, be fluorescein (absorption maximum of 488 nm), dichloro-fluorescein (absorption maximum of 525 nm), hexachloro-fluorescein (absorption maximum of 529 nm), BODIPY™ (absorption maximum of 530 nm), ROX (absorption maximum of 550 nm), tetramethylrhodamine (absorption maximum of 550 nm), rodamine X (absorption maximum of 575 nm), Cy2™ (absorption maximum of 505 nm), Cy3™ (absorption maximum of 550 nm), Cy5™ (absorption maximum of 650 nm), Cy7™ (absorption maximum of 750 nm), IRD40 (absorption maximum of 785 nm), and the like, and further described in Smith et al. (1986) Nature 321: 647–649.

Figure 2A:
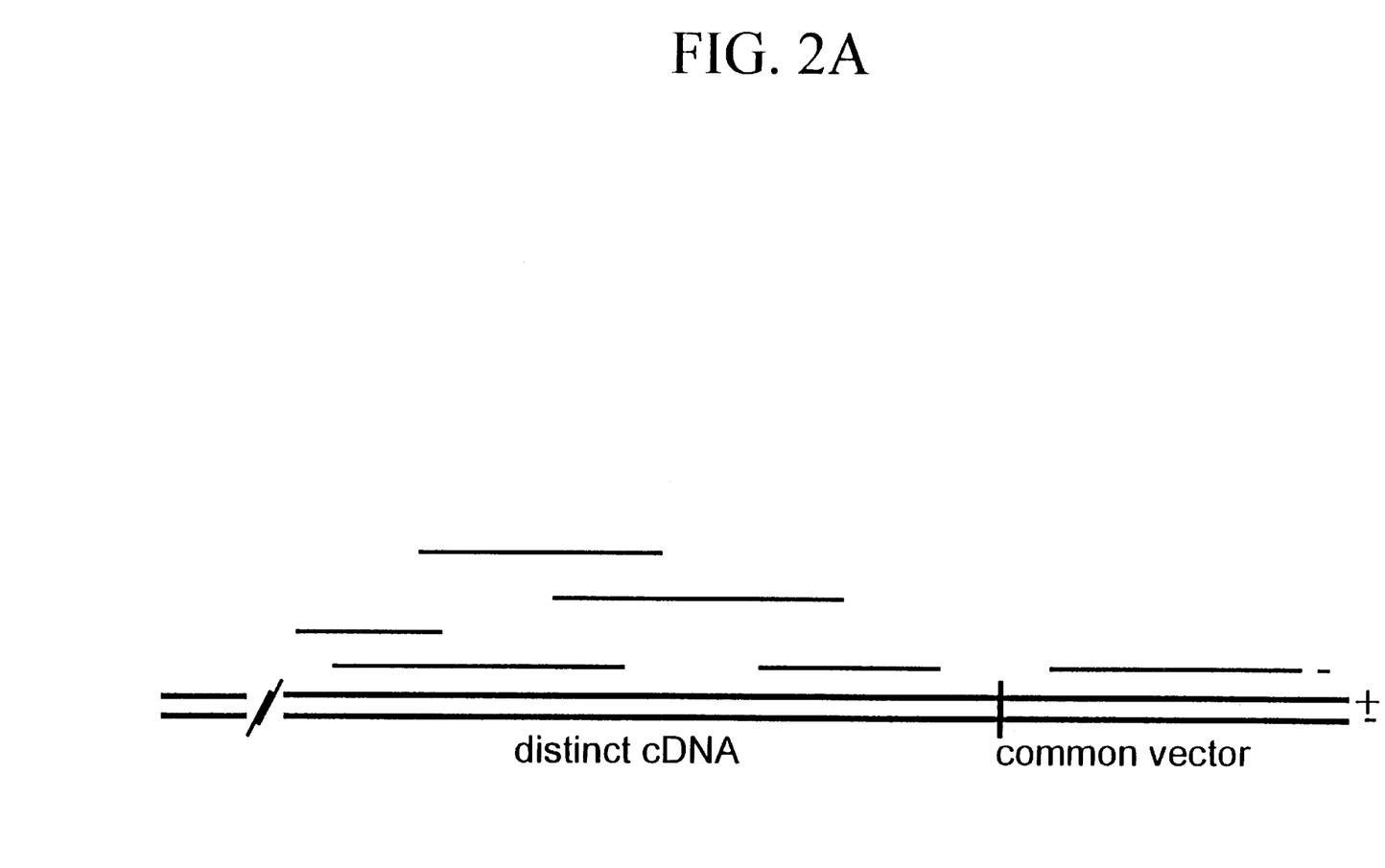
FIG. 2A provides a schematic representation of co-hybridization with an antisense standard probe.
Figure 2B:
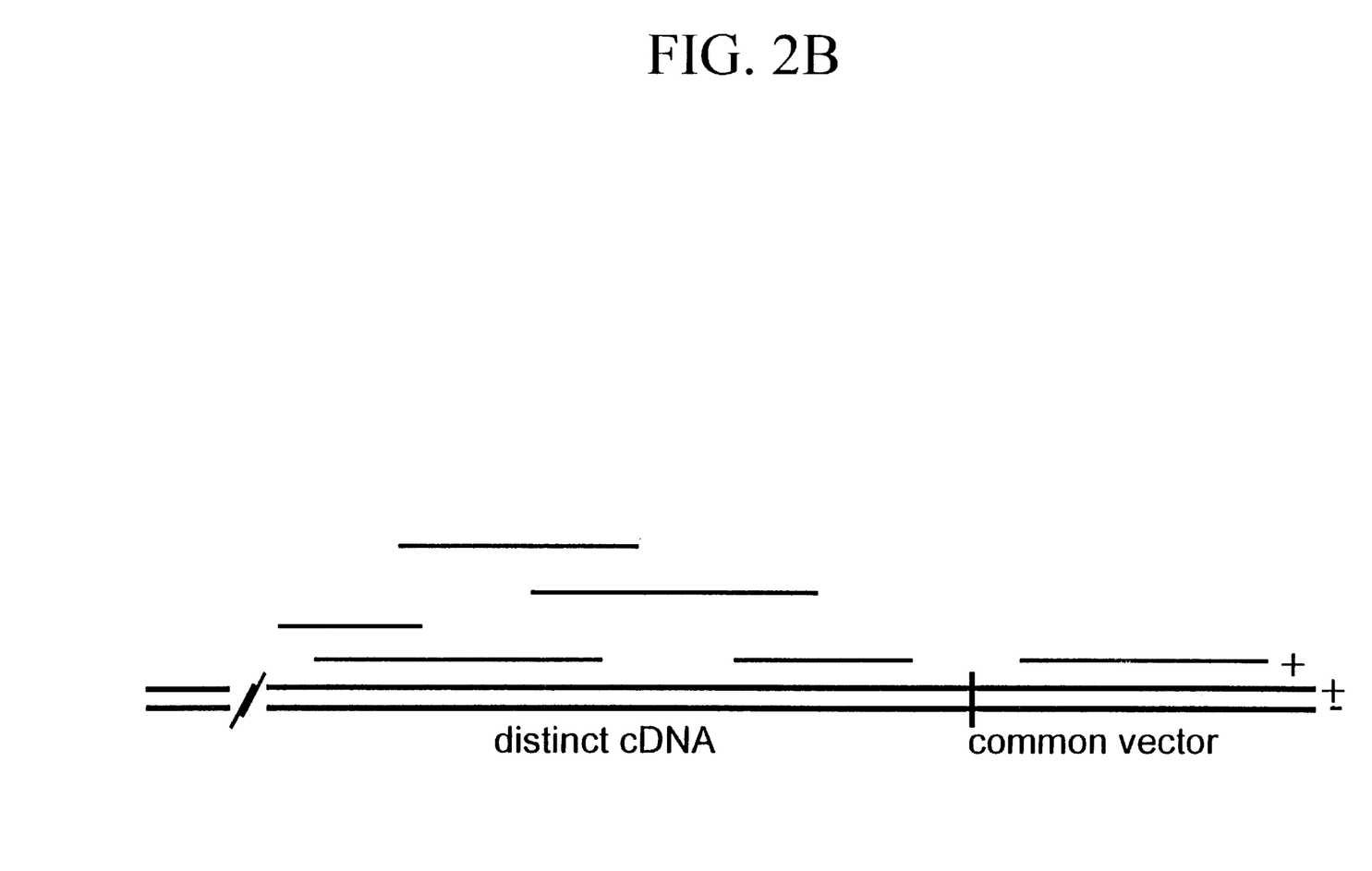
FIG. 2B provides a schematic representation of co-hybridization with an sense standard probe.
Figure 2C:
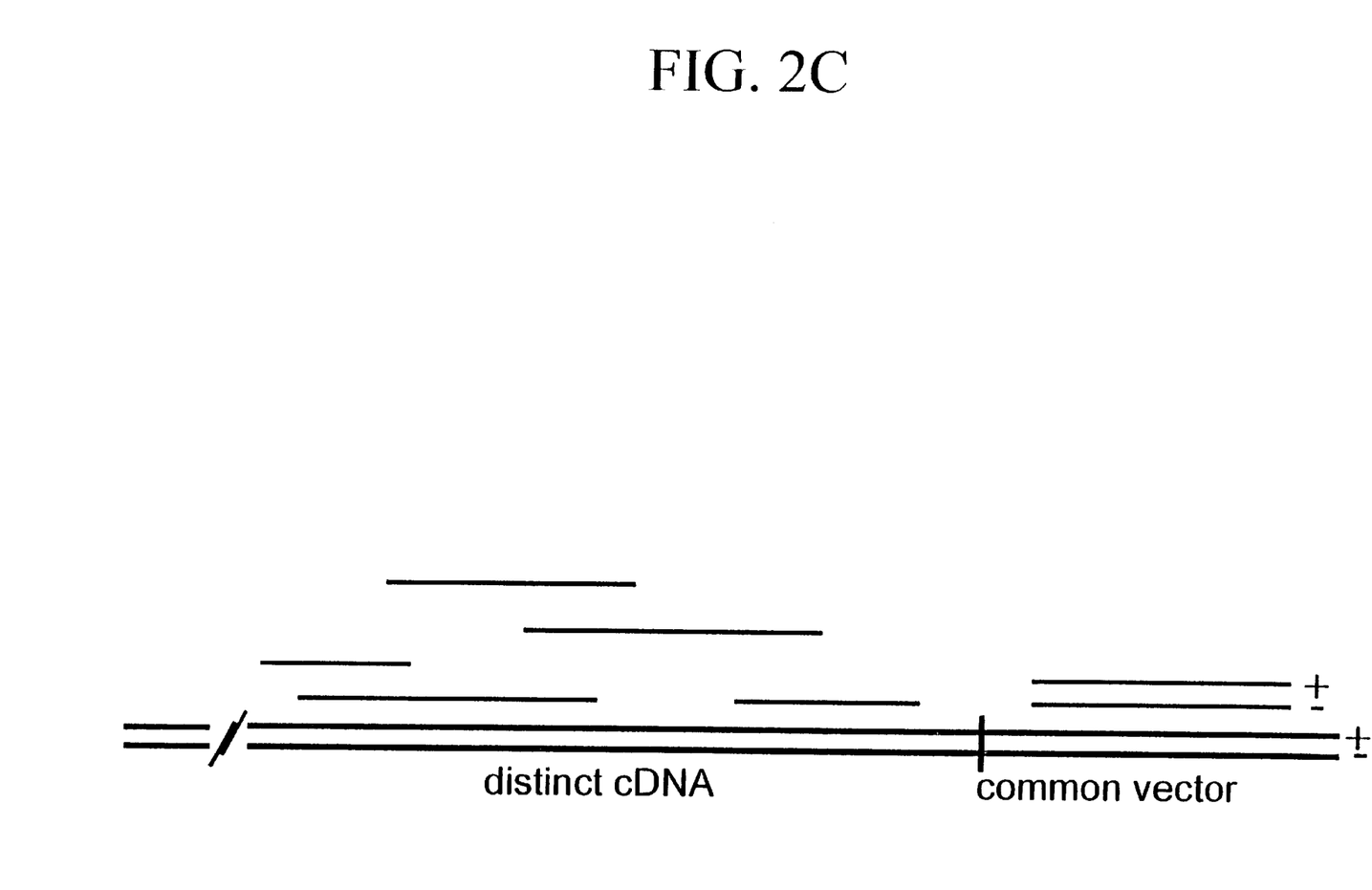
FIG. 2C provides a schematic representation of co-hybridization with sense and antisense standard probes.
Figure 2D:
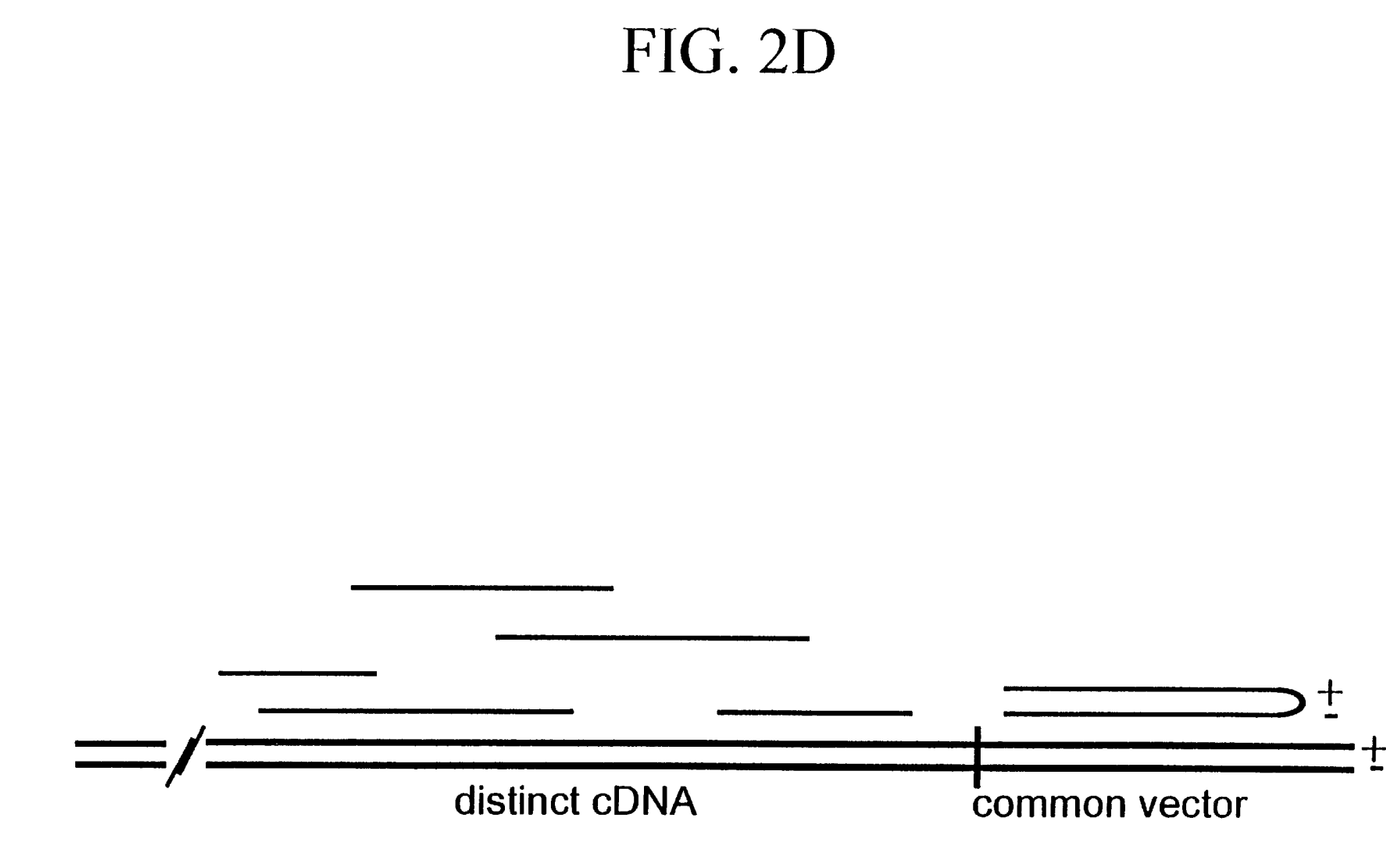
FIG. 2D provides a schematic representation of co-hybridization with a hairpin standard probe.

Similarly, cDNA corresponding to the standard polynucleotide targets is produced and differently labeled. As illustrated in FIGS. 2A–C, the independently detectable standard probes can be single stranded, double stranded, or hairpins. The double stranded probes consist of both the sense and the antisense complement to the standard sequences where both strands have the same label. The detectable probes and the independently detectable single and double stranded complements to the standard sequences are contacted with the microarray, either sequentially or concurrently, under conditions sufficient for the probe sequences to hybridize to the complementary polynucleotides of the microarray. The sense and antisense complements to the standard target sequence can be present in any stoichiometry, but are generally present in approximately equimolar concentrations in the reaction fluid. In addition, the sense and antisense sequences can be covalently attached using a variety of methods. In one method, the two strands can be linked as a hairpin, as illustrated in Example 4, below. Additionally, the strands can be synthesized as a double hairpin and/or ligated to form a closed dumbell (Annu. Rev. Bioohys, Biomol. Struct., 25, 1–28, (1996)). Other methods include covalently coupling the sense and antisense strands using standard chemistry approaches. One such method of coupling incorporates linker-arms in the complementary strands, where the linker-arm is modified to react with a functional moiety introduced into the complementary strand. Convenient moieties include alkylamines introduced in one strand and active esters, active amides, active imines, aldehydes, bromoacetamides, thiocyanates, and the like in the other strand, as is well known to one skilled in the art. Other convenient coupling moieties include thiols in one strand and disulfides, maleimides, and bromoacetamides in the other strand (see for example, Bioconjugate Chemistry, 1, 165–187 (1990) and references contained therein). Such couples can be positioned at one end, the other end, at both ends, or across an interior portion of the two strands.

The targets and probes are used in a method for immobilizing a polynucleotide probe comprising the steps of: combining the probe with a polynucleotide target stably associated with a surface of a solid support, wherein one of the probe and target is double-stranded comprising complementary strands, and the other is single-stranded having complementarity with one of the complementary strands, under conditions wherein the probe and target hybridize and the probe is thereby immobilized.

In another embodiment, the method comprises the step of combining the probe with a polynucleotide target stably associated with a surface of a solid support, wherein the probe and target are double-stranded comprising complementary strands and have complementarity, under conditions wherein the probe and target hybridize and the probe is thereby immobilized. The probe and target are preferably heteropolymers of purines and pyrimidines.

In a particular embodiment, the method further comprises the step of isolating or releasing the immobilized probe from the solid support. In another particular embodiments, the method further comprises the step of amplifying the immobilized probe. In another particular embodiment, the method further comprises the step of amplifying the immobilized probe and then detecting resultant amplified probe. In a more particular embodiment, the method further comprises the steps of releasing and amplifying the probe to produce a labeled, amplified double-stranded probe, hybridizing the labeled probe to a target polynucleotide to immobilize the labeled probe and detecting the labeled probe, particularly wherein the probe is double-stranded and target is single-stranded.

Suitable hybridization conditions are well known to those of skill in the art and reviewed in WO 95/21944 to Maniatis et al. (supra). Incubation conditions are adjusted so that hybridization occurs with precise complementary matches or with various degrees of less complementarity. After removal of nonhybridized probes, a scanner is used for detection or visualization to determine the levels and patterns of fluorescence. A detection system may be used to measure the absence, presence, and amount of hybridization for all of the distinct sequences simultaneously.

In detecting or visualizing the hybridization pattern, the intensity or signal value of the label on the nucleic acids probe, and the intensity or signal value of the different label from the standard sequence probes is obtained. The intensity or signal value corresponding to the standard sequence represents the total amount or unit value of hybridization in the experiment, and serves as a control. The signal for each element of the microarray is measured and compared to the unit value. The method of the invention thus uses two colors (channels) for characterizing the results of hybridization. The color from the standard targets becomes an element-specific control against which the color from the probe can be calibrated or numerically adjusted. The invention thus provides quantitative information on each element of the microarray. Another advantage of the invention is that the hybridization of the probe sequences and the standard sequences is not competitive, thereby reducing noise in the results.

The hybridization pattern can be used to determine quantitative information about the genetic profile of the nucleic acids in the sample that was contacted with the array to generate the hybridization pattern, as well as the physiological source from which the labeled sample nucleic acid was derived. The data provides information about the physiological source from which the sample nucleic acid were derived, such as the types of genes expressed in the tissue or cell which is the physiological source, as well as the levels of expression of each gene, particularly in quantitative terms.

The present method can be used in comparing nucleic acid samples from two or more physiological sources to identify and quantify differences between the patterns thereby providing data on the differential expression of a particular gene in the physiological sources being compared. Thus the methods of the invention find use in differential gene expression assays for the analysis of a diseased and normal tissue, analysis of a different tissue or subtissue types, and the like. Thus, this data may be used for large scale correlation studies on the sequences, mutations, variants, or polymorphisms among samples.

In an alternative embodiment, the standard polynucleotide sequences are doped into the sample containing the distinct polynucleotides with controlled stoichiometry. The standard sequences and the distinct polynucleotides are thus not covalently attached. The standard sequences, preferably having sequences different than the sequences of the microarray elements, are present in known amounts and can thus be used as a calibrating agent in subsequent analysis. In the method, the sample containing the polynucleotides for use in the fabrication of the microarray is spiked with the standard sequences. The standard sequences serve as a normalization control. The sample, containing the polynucleotides from the gene and the standard sequences, is then deposited on the microarray, hybridized with the labeled sample and differently labeled standard probes, and the hybridization pattern analyzed as described above.

Also provided are kits for carrying out the invention, where such kits include one or more microarrays fabricated such that the elements contain the distinct polynucleotide sequences and the standard polynucleotide sequence, labeled standard complements to the standard sequences and instructional material for carrying out the subject methodology. The kit may also include one or more additional components necessary for carrying out the gene expression of the subject invention, where such additional components include enzymes, e.g. polymerases, reverse transcriptases, endonucleoses, dNTPs, buffers, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperatures, etc.) but some experimental errors and deviations should be accounted for. Unless indicated otherwise, parts are parts by weight, molecular weight is weight average molecular weight, temperature is in degrees Centigrade, and pressure is at or near atmospheric.

Unless otherwise indicated, the cDNA microarrays, made according to U.S. Pat. No. 5,807,522 to Brown et al., were provided by Incyte Genomics, Inc. These substrates provide a polycationic surface, e.g. with polylysine, polyarginine, polyethylenimine, etc. The oligonucleotides were synthesized and purified by Operon Technologies, and used without further purification.

Example 1

The 59 mer oligonucleotide of SEQ ID NO:1, having complementarity to the vector portion of the arrayed cDNA, was synthesized and labeled with a 5' Cy3 fluorescent dye.

5'TTCGAGCTTGGCGTAATCATGGTCATAGCT GTTTCCTGT-
GTGAAATTGTTATCCGCTCA3'        SEQ ID NO:1

The labeled oligonucleotide of SEQ ID NO. 1 was hybridized to the cDNA microarray. The hybridization chamber contained approximately 25 uL of the labeled oligonucleotide at a concentration of about 10 ng/uL, and a complex mRNA labeled with a Cy5 fluorescent dye. Following the hybridization reaction at 60° C., the microarray was washed twice. The first wash solution consisted of 1×SSC and 0.1% SDS, while the second wash solution consisted to 0.1×SSC and 0.2% SDS. The microarray was washed in each of the solutions for 10 min. at 45° C. and exposed to fluorescent light to detect the hybridization pattern. Non specific hybridization was not observed. The Cy3 signal corresponding to SEQ ID NO.:1 was used to quantify the hybridization of mRNA to the corresponding sequences on the microarrays.

Example 2

The procedure described in Example 1 was repeated, except SEQ ID NO:2 was used instead of SEQ ID NO:1.

5'TGAGCGGATAACAATTTCACACAGGAAACA GCTATGAC-
CATGATTACGCCAAGCTCGAA3'        SEQ ID NO:2

SEQ ID NO:2 was the reverse complement of SEQ ID NO:1. Results similar to those described in Example 1 were obtained.

Example 3

The procedure described in Example 1 was repeated, except approximately 10 ng/uL of the labeled SEQ ID NO.:1 and approximately 10 ng/uL of the labeled SEQ ID NO.:2 in a total volume of approximately 25 uL were placed in the hybridization chamber concurrently. Non-specific hybridization was not seen. In the experiment, four different GEM arrays were used for hybridization to the same sample, and the results of hybridization were analyzed. Table I shows the percentage of element groups that had less than 15% cv.

| GEM | Reproducibility using the method of Example 1 | Reproducibility using the method of Example 3 |
|---|---|---|
| 132Q9273 | 84.15584 | 90.90909 |
| 132X9274 | 93.78109 | 91.54229 |
| 13249275 | 74.73118 | 83.06452 |
| 132B9276 | 73.31606 | 74.87047 |
| Average: | 81.49605 | 85.09659 |
| stdev | 8.226063 | 6.782977 |

The results indicated that a 1:1 mixture of the sense and the anti-sense strands improved the signal to noise ratio by about 2 to 3 fold over that observed in Examples 1 and 2.

Example 4

To test for the ability of a hairpin to hybridize to vector sequences, the procedure described in Example 1 was repeated, except approximately 25 uL of the labeled SEQ ID NO.:3 at a concentration of about 16 ng/uL was placed in the hybridization chamber and complex Cy5 labeled MRNA probe sample was omitted.

5'GTAATCATGGTCATAGCTGTTTCCTGT-
GTGAAATTGTTATCCGCTCATTT

3'CATTAGTACCAGTATCGACAAAGGACA-
CACTTTAACAATAGGCGAGTTT        SEQ ID NO:3

The hairpin structure of Seq. ID 3 consisted of the first 47 bases of SEQ ID NO.:1 and the last 47 bases of SEQ ID NO.:2 connected together by the 5 thymine bases to form the loop of the hairpin. The results of hybridization are analyzed as described in Example 1. Non-specific hybridization was not seen, and the hairpin structure had specific hybridization intensities and morphologies that were similar to those observed for SEQ ID NO. 1 and 2 in Examples 1 to 3 above.

Example 5

To utilized the hairpin for normalization, the procedure described in Example 1 is repeated, except approximately 25 uL of the labeled SEQ ID NO.:3 at a concentration of about 16 ng/uL is placed in the hybridization chamber along with a complex mRNA labeled with a Cy5 fluorescent dye. The results of hybridization are analyzed as described in Example 1. Non-specific hybridization is not seen, and the signal to noise ratio is similar to those measured in Example 3. The signal corresponding to the hybridization of the hairpin structure to the microarray is used to quantify the signal from the probes.

Example 6

Figure 3:
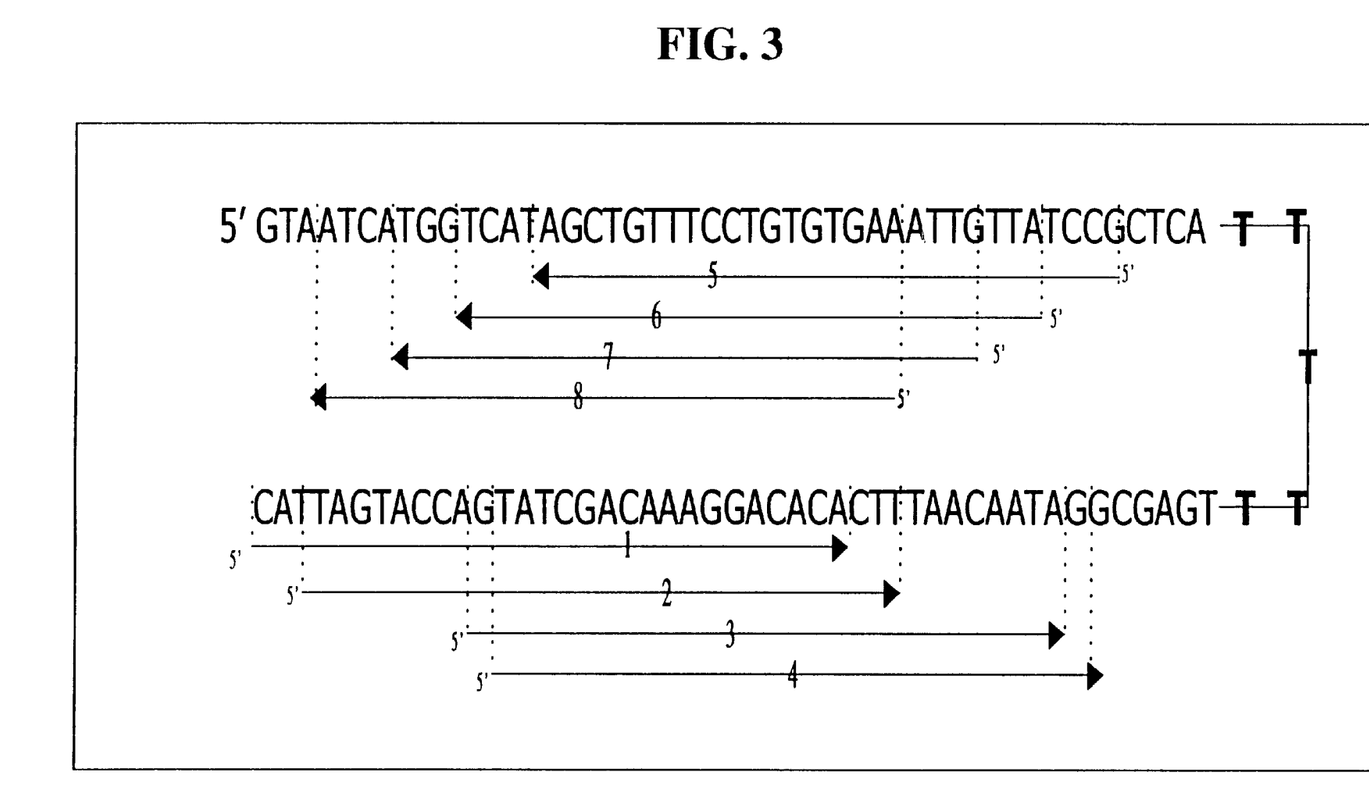
FIG. 3: The structure of the hairpin and the design of 30-mers complementary to the hairpin (SEQ ID NO:3). Polynucleotides 1–4 are complementary to the 3' arm of the hairpin; polynucleotides 5–8 are complementary to the 5' arm (see, Example 6).
Figure 4:
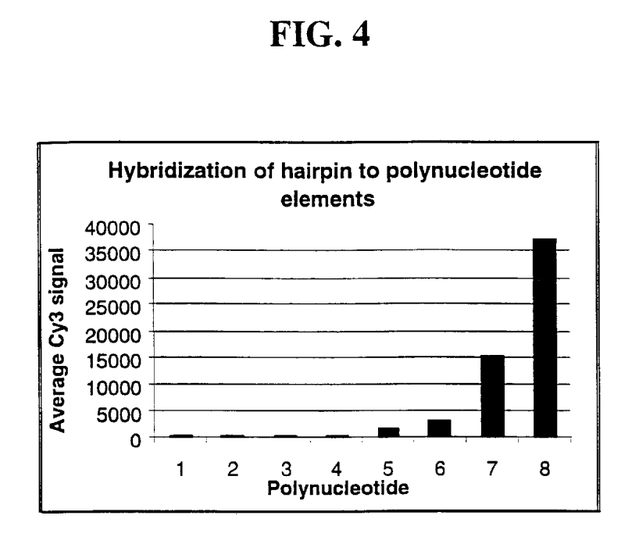
FIG. 4. Hybridization signal obtained at different elements with the hairpin (see, Example 6).

To test for the ability of a hairpin to hybridize with polynucleotide elements, the procedure described in Example 4 was repeated with array elements consisting of chemically synthesized 30 mers. Polynucleotide arrays were created as follows:

5' amino-linked 30-mers were synthesized by Operon Technologies (Alameda, Calif.). These sequences were designed to tile across the 47-mer sequence of each arm of the hairpin as illustrated in FIG. 3. These polynucleotides were arrayed at 25 μM in 3×SSC to P-glass slides (an array glass surface that had been covalently coated with polyethylenimine and activated with cyuranic acid chloride for covalent attachment). See co-pending application Ser. No. 09/532,419 entitled Polymer Coated Surfaces for Microarray Applications. Arrays were post-processed by submerging in the following succession of solutions: 0.2% SDS at room temperature for 2 minutes, three 1-minute washes in room temperature dH$_2$O, 20 minutes in 0.25% casein 1×PBS at 60°, 0.2% SDS at room temperature for 5 minutes, two 2-minutes washes in room temperature dH$_2$O, 2 minutes in boiling (95°–100°) dH$_2$O. The Cy3 labeled hairpin was hybridized at 10 ng/µl in 5×SSC 0.2%SDS 5 hr at 60° C. After hybridization arrays were washed first in 1×SSC, 0.1%SDS, 1 mM DTT for 10 minutes at 45° C., then 0.1×, 0.2%SDS, 1 mM DTT for 3 minutes at 25°. The arrays were imaged by using a GenePix™ scanner (Foster City, Calif.) with a 10 micron resolution. The signal was converted into 16-bits-per-pixel resolution, yielding a 65,356 count dynamic range with a PMT setting of 500 mV. Incyte GEMTool™ software (Incyte Genomics, Inc, Palo Alto, Calif.) was used for image analysis. The hybridization signal obtained at different elements with the hairpin is shown in FIG. 4. Signals were corrected for local background.

The elements complementary to the 3' arm of the hairpin hybridized poorly (polynucleotides 1–4), while all of the elements complementary to the 5' arm of the hairpin (polynucleotides 5–8) hybridized moderately to very well. Due to the complementarity of the hairpin strands, this indicates that the single strand elements corresponding in sequence to the 3' end of the hairpin probe show a strong preference for association.

Example 7

Figure 1:
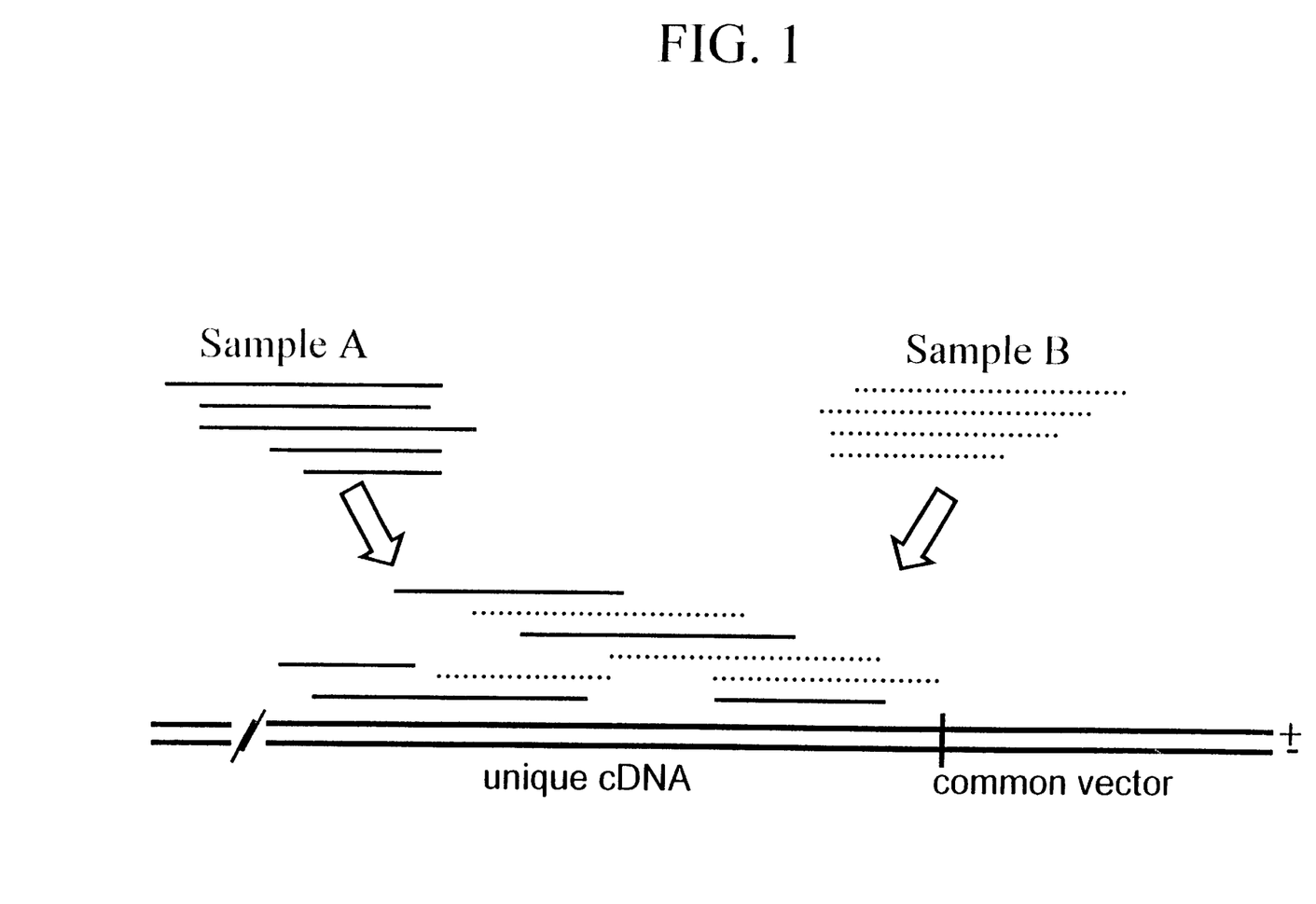
FIG. 1 provides a schematic representation of the labeling approach of the method using two colors.
Figure 5:
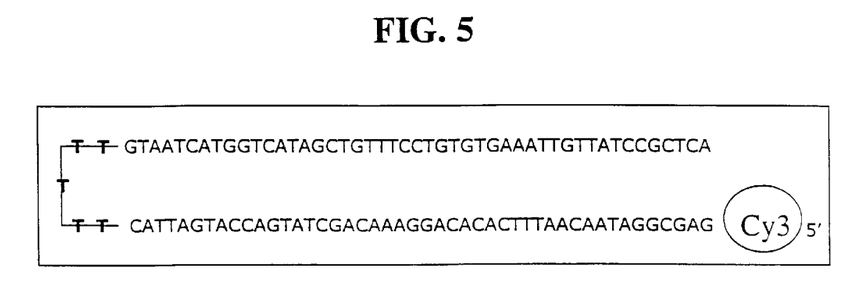
FIG. 5. The structure of the flipped hairpin (SEQ ID NO:4; see Example 7).

To test the specificity of a flipped hairpin, a reversed hairpin, was synthesized and hybridized as described in Example 6. This hairpin is a variation on the hairpin shown in FIG. 1 in that the arms are reversed (see FIG. 5). Oligos 1–4 still hybridize to the strand pictured on the bottom, although this is now the 5' strand. Oligos 5–8 hybridize to what is now the 3' strand. The flipped hairpin was hybridized on polynucleotide arrays as described in Example 6.

Figure 6:
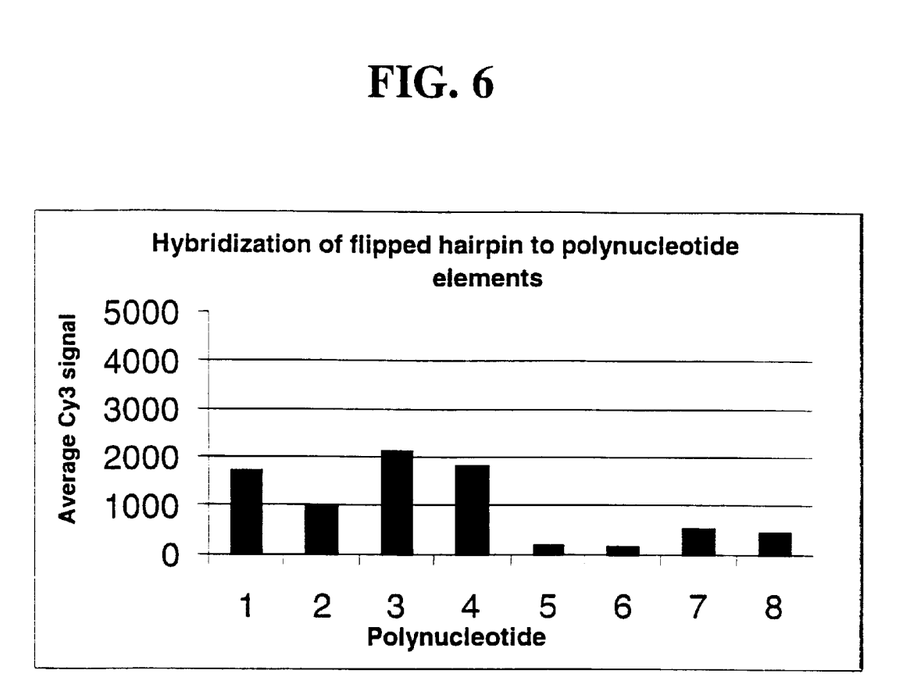
FIG. 6. The hybridization signal obtained at different elements with the flipped hairpin (see, Example 7).

Hybridization with the flipped hairpin shows preference for association with elements complementary to the opposite strand compared to that depicted in Example 6 as shown in FIG. 6. These elements likewise (compared to Example 6) correspond in sequence to the 3' end of the hairpin probe.

Example 8

Figure 7:
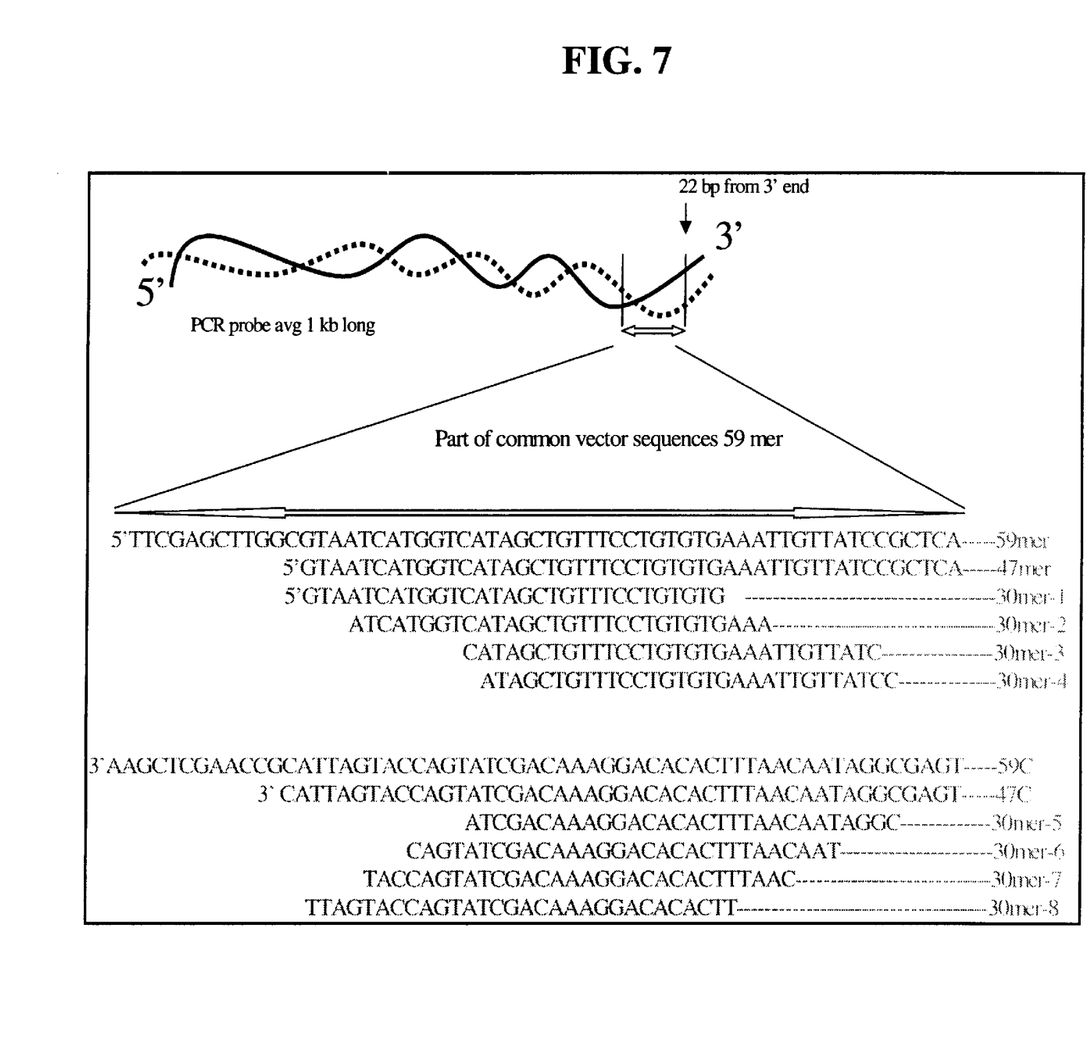
FIG. 7. The sequence of the PCR probe vector sequence in relation to the 30 mer, 47 mer (SEQ ID NO:2), and 59 mer (SEQ ID NO:1) single stranded element sequences. The sequences of the elements are as indicated (see, Example 8).

To test for the ability of long DNA duplexes (500–2.5 kb) to associate with single stranded polynucleotide array elements, long duplex probes were labeled using a standard nick translation kit (Promega Corporation, Madison Wis.) with modifications. Six 96 well plates of PCR products, containing common a vector sequence were pooled at a concentration of 100 ng/µl and nick translated. The array elements: 30 mer, 47 mer, and 59 mer sequences, as well as their complements, correspond to a common vector sequences present on the PCR products. The 59 mers and 47 mers start 22 bases from the 3' terminus, and the 30 mers are between 26 and 37 bases from the 3' end (See FIG. 7). The PCR products are 750 bp to 2.5 kb in length.

Two modifications were made in the nick-translation protocol as follows. Fifty percent of the dUTP was substituted by Cy-3 labeled dUTP and the reaction was run for only 1 hour. The PCR probes were then purified by ethanol precipitation. These modifications produced well-preserved double stranded DNA labeled with Cy3.

Arrays were prepared as described in Example 6 with the exception that 47 mer and 59 mer sequences were also included together with their complements. Hybridizations were performed in a solution of 5×SSC/0.2% SDS/1 mM DTT for 6 hours at 60° C. using 2.5 ng/µl of PCR duplex probe. The 20-ul probe (50 ng) resuspended in hybridization buffer were loaded for hybridization. The probe was applied to the array and covered with a 22-mm$^2$-glass cover slip, and placed in a sealed chamber to prevent evaporation and incubated at 60° C. After the hybridization, the arrays were washed for 10 minutes in 1×SSC/0.1%SDS/DTT at 45° C. then for 5 minutes in 0.1×SSC/0.2%SDS/DTT at 25° C. The ds PCR probe hybridized preferentially to 59 mer, 47 mer and 30 mer than their complementary sequences. The results are listed in Table II. The single strand elements that correspond to the 3' end of the duplex probe show a strong preference for association.

TABLE II

| Elements | Signal Intensity | Strand Preference Ratio |
|---|---|---|
| 59 mer/59 mer complement | 23017/1327 | 17 |
| 47 mer/47 mer complement | 17651/1097 | 16 |
| 30 mer/30 mer complement | 2550/373 | 6.8 |

Example 9

To determine the ability of single stranded probes to hybridize to duplex PCR elements, a single strand probe 59 mer and its complement were synthesized and labeled on the 5' end ( Operon Technology, Alameda Calif.). Ten ng of probe in 20 µl 5×SSC/0.2% SDS/1 mM DTT was used for hybridization. The average signal from the 59 mer-Cy3 hybridization was 5672 and the corresponding signal from its labeled complement was 93. The strand preference ratio is about 61 as shown in Table III. In this example the probe that corresponds to the 3' sequence of the target duplex element shows a strong preference for association. For comparison, the PCR duplex was denatured and arrayed in 100 mM Na$_2$CO$_3$. The resulting ratio of denatured strands are about 2.6, indicating that when the strands are largely denatured, they hybridize much more equivalently to there corresponding complementary sequences.

TABLE III

| Array condition | 59 mer-Cy3 | 59-Cy3 complement | Strand preference ratio |
|---|---|---|---|
| Duplex PCR (2×SSC) | 5672 | 93 | 61 |
| Duplex PCR (100 mM Na$_2$CO$_3$) | 10614 | 4062 | 2.6 |

Example 10

To determine the ability of metal ions to increase the association of single stranded structures with double stranded structures on solid surfaces, hybridization reactions were carried out in the presence of low concentrations of metal ions. Double stranded labeled PCR probes were hybridized at 2.5 ng/µl and processed as described in Example 8 above, with the exception that Zn$^{++}$ or Ni$^{++}$ were added at a concentration of 1.5 mM. As shown in Table IV, the metal ions enhanced the hybridization signals on oligomer elements 30 mer, 47 mer and 59 mer elements. The effect was particularly significant for the 30 mer elements that formed the least stable complexes in the absence of the metal. Enhanced hybridization signals are similarly obtained with other metal ions, including Ca$^{++}$, Fe$^{++}$, Fe$^{+++}$, Mg$^{++}$, K$^+$, Co$^{++}$, Co$^{+++}$, as well as rare earth metals.

TABLE IV

| | Hybridization signal intensity on elements | | | |
|---|---|---|---|---|
| | 30 mer | 47 mer | 59 mer | cDNA |
| 5xSSC | 976 | 15119 | 20110 | 353 |
| 4xSSC/1.5 mM $Zn^{++}$ | 4975 | 21519 | 24207 | 526 |
| 4xSSC/1.5 mM $Ni^{++}$ | 1420 | 22101 | 20497 | 404 |

Example 11

To test for the ability of a hairpin to hybridize to duplex vector sequences, the hybridization described in Example 4 was performed on nondenatured arrays. PCR fragments were amplified, purified by standard filtration methods, dried down and resuspended in 2xSSC without a heat denaturation step. These products were then arrayed, such that the elements were double stranded. Approximately 25 ul of the labeled SEQ ID NO.3 at a concentration of about 10 ng/ul was placed in the hybridization chamber. The results of hybridization were analyzed as described in Example 1. Non specific hybridization was not seen, and the hairpin structure had specific hybridization intensities and morphologies that were similar to those observed for SEQ ID NO. 1 and 2 in Examples 1 to 3 above.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for immobilizing a polynucleotide probe comprising the step of:
   combining the probe with a first polynucleotide target stably associated with a surface of a first solid support, wherein the probe and target comprise respectively first and second double-stranded portions, each comprising complementary strands, wherein the first and second double-stranded portions have complementarity to each other, under conditions wherein the first and second double-stranded portions hybridize and the probe is thereby immobilized.

2. A method according to claim 1, further comprising the step of detecting specific hybridization of the probe and the target.

3. A method according to claim 1, further comprising the step of releasing the immobilized probe.

4. A method according to claim 1, further comprising the step of amplifying the immobilized probe.

5. A method according to claim 1, further comprising the step of amplifying the immobilized probe and then detecting resultant amplified probe.

6. A method according to claim 1, further comprising the steps of:
   releasing and amplifying the probe to produce an amplified, labeled probe comprising a third double-stranded portion,
   hybridizing the labeled probe to a fourth double-stranded portion of a second polynucleotide target stably associated with a surface of a second solid support to immobilize the labeled probe; and
   detecting the labeled probe.

7. A method according to claim 1, further comprising the steps of:
   releasing and amplifying the probe to produce a labeled, amplified probe comprising a third double-stranded portion;
   hybridizing the amplified probe to a second polynucleotide target to immobilize the labeled probe; and
   detecting the labeled probe, wherein the second target is single-stranded.

8. A method according to claim 1, wherein the complementary strands of at least one of the probe and the target are noncovalently linked.

9. A method according to claim 1, wherein the complementary strands of at least one of the probe and the target are covalently linked.

10. A method according to claim 1, wherein the probe comprises a detectable label.

11. A method according to claim 1, wherein the target and solid support are of a microarray.

12. A method according to claim 1, wherein the conditions include an amount of a metal ion sufficient to enhance hybridization of the target and probe.

13. A method according to claim 1, wherein the conditions include an amount of a metal ion sufficient to enhance hybridization of the target and probe, wherein the metal ion is selected from the group consisting of $Zn^{++}$, $Ni^{++}$, $Ca^{++}$, $Fe^{++}$, $Fe^{+++}$, $Mg^{++}$, $K^+$, $Co^{++}$ and $Co^{+++}$.

14. A method according to claim 1, wherein the solid support comprises a polycationic surface.

15. A method for immobilizing and detecting a polynucleotide probe, comprising the steps of:
   contacting a polynucleotide target comprising a first double-stranded portion and which is stably associated with a surface of a solid support, with a polynucleotide probe comprising a second double-stranded portion; and
   detecting specific hybridization of the first and second portions.

16. A method according to claim 15, wherein the second double-stranded portion comprises noncovalently linked complementary strands.

17. A method according to claim 15, wherein the second double-stranded portion comprises covalently linked complementary strands.

18. A method according to claim 15, wherein the second double-stranded portion comprises covalently linked complementary strands and is part of a hairpin structure.

19. A method according to claim 15, wherein the second double-stranded portion comprises covalently linked complementary strands, linked through a first coupling moiety on one strand and a second coupling moiety on the second strand.

20. A method according to claim 15, wherein the second double-stranded portion comprises covalently linked complementary strands, linked through a first coupling moiety on one strand and a second coupling moiety on the second strand, wherein
   (a) the first coupling moiety is an alkylamine and the second coupling moiety is selected from an active ester, amide, imine, aldehyde, bromoacetamide and thiocyanate; or
   (b) the first coupling moiety is a thiol and the second coupling moiety is selected from a disulfide, maleimides and bromoacetamides.

21. A method according to claim 15, wherein the probe comprises a detectable label.

22. A method according to claim 15, wherein the target and solid support are of a microarray.

23. A method according to claim 15, wherein the solid support comprises a polycationic surface.

24. A method according to claim 1 wherein the target and probe are heteropolymers of purines and pyrimidines.

25. A method according to claim 15 wherein the target and probe are heteropolymers of purines and pyrimidines.

* * * * *

UNITED STATES PATENT AND TRADEMARK OFFICE
CERTIFICATE OF CORRECTION

PATENT NO. : 6,448,013 B1
DATED : September 10, 2002
INVENTOR(S) : Arnold et al.

It is certified that error appears in the above-identified patent and that said Letters Patent is hereby corrected as shown below:

<u>Title page,</u>
Item [75], please replace "Bieldanes" with -- Bjeldanes --

Signed and Sealed this

Twelfth Day of August, 2003

JAMES E. ROGAN
*Director of the United States Patent and Trademark Office*